United States Patent [19]

Sato et al.

[11] 4,144,279
[45] Mar. 13, 1979

[54] ARALKYLATION OF ALKYLBENZENES

[75] Inventors: Atsushi Sato; Isoo Shimizu, both of Yokohama; Eiichi Matsuzaka, Tokyo, all of Japan

[73] Assignee: Nippon Petrochemicals Company, Limited, Tokyo, Japan

[21] Appl. No.: 898,328

[22] Filed: Apr. 20, 1978

[30] Foreign Application Priority Data

Apr. 27, 1977 [JP] Japan .................................. 52-47778

[51] Int. Cl.² ............................................. C07C 3/10
[52] U.S. Cl. ............................ 260/668 R; 252/455 R; 208/139
[58] Field of Search ............................ 260/668, 649; 252/455 R

[56] References Cited

U.S. PATENT DOCUMENTS 3,069,478  12/1962  McLaughlin .................... 260/649 R Primary Examiner—Veronica O'Keefe
Attorney, Agent, or Firm—Scully, Scott, Murphy & Presser

[57] ABSTRACT

The present invention provides a process for aralkylation of alkylbenzenes wherein an alkylbenzene or alkylbenzenes containing in the substituent alkyl group or groups from 1 to 4 carbon atoms in total is aralkylated with at least one styrene selected from the group consisting of styrene, vinyltoluenes and α-methylstyrene which comprises carrying out the reaction by continuously feeding to a catalyst layer the above-mentioned alkylbenzene or alkylbenzenes and styrene sources in liquid phase at a temperature from 100° C. to 200° C., said catalyst layer being filled with synthetic silica-alumina containing from 20% by weight to 50% by weight alumina that has been calcined at a temperature in the range from 450° C. to 600° C.

3 Claims, 1 Drawing Figure

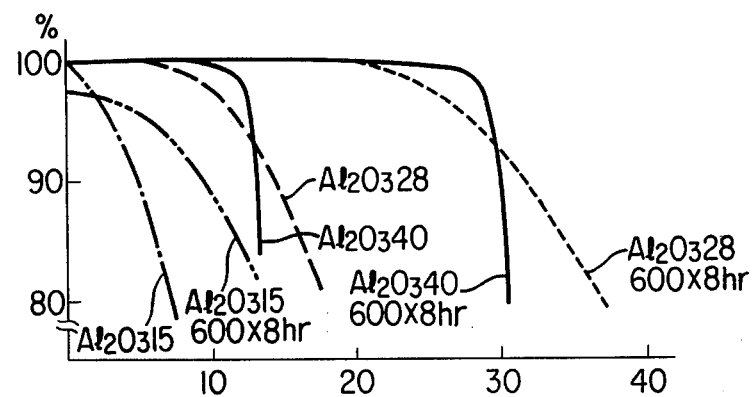

ARALKYLATION OF ALKYLBENZENES

BACKGROUND OF THE INVENTION

1. Field of the Invention

This invention relates to a process for aralkylating alkylbenzenes with styrenes. It is more particularly concerned with a process for catalytically aralkylating alkylbenzenes by continuously feeding an alkylbenzene and a styrene to a catalyst layer filled with synthetic silica-alumina that has been subjected to calcination at temperature between 450° C. and 600° C.

2. Description of the Prior Art

Alkylation reactions between an alkylbenzene and an olefin which are the most important reactions in chemical industry find many uses. In cases where aromatic olefins such as styrene (termed styrenes hereinbelow) are employed as the olefin the reaction is called an "aralkylation" reaction. Non-condensed polycyclic aromatic hydrocarbon compounds from the aralkylation between an alkylbenzene and a styrene which have excellent properties in terms of compatibility, heat resistance, lubricity and electric properties are synthetic oil suitable for wide uses such as those as plasticizer, high-boiling solvent, heat medium, electric insulating oil, working oil and lubricant. The desired aralkylated alkylbenzenes that are the synthetic oil of desirable properties for these uses cannot be produced in a high yield due to liability of styrenes to be polymerized when one of the conventional alkylation catalyst is used.

As the heretofore disclosed aralkylation catalyst are mentioned concentrated sulfunic acid proposed in British Pat. No. 977,322 and acidic solid acids proposed in U.S. Pat. No. 3,069,478. The process with sulfuric acid, when operated on an industrial scale, requires not only high cost for the aftertreatment such as the water required for the neutralization to remove the catalyst after completion of the reaction but also means for preventing corrosion of the equipment as well as environmental pollution from the discharged water. On the other hand, prior art technique by the use of clay mineral catalysts such as acid clay represents batch processes of the catalytic reaction only.

It has been found that the synthetic silica-alumina containing from 7% to 15% alumina disclosed in U.S. Pat. No. 3,069,478 is unfitted in practice for use in the continuous process, owing to its short life, although, as described in detail in the patent specification, it is effective in the batch reaction.

SUMMARY OF THE INVENTION

We have now found catalysts and preparation of those catalysts which are most suitable for use in the fixed-bed catalytic continuous reaction most preferable from the industrial point of view.

The present invention provides a process for aralkylation of alkylbenzenes wherein an alkylbenzene containing in the side of chains from 1 to 4 carbon atoms in total is aralkylated with at least one styrene selected from the group consisting of styrene, vinylstyrenes and α-methylstyrene which comprises carrying out the reaction by continuously feeding to a catalyst layer a mixture of the above-mentioned alkylbenzene and styrene in liquid phase at a temperature from 100° C. to 200° C., said catalyst layer being filled with synthetic silica-alumina containing from 20% by weight to 50% by weight alumina that has been calcined at a temperature in the range from 450° C. to 600° C.

BRIEF DESCRIPTION OF THE DRAWING

FIG. 1 of the attached drawing represents a graph indicating relationship between the calcination conditions and the life of the catalyst for the catalyst employed in the aralkylation of alkylbenzenes according to the present invention with various alumina contents. In FIG. 1 the axis of abscissas represents reaction days and the axis of ordinates reaction percentage. $Al_2O_3{}^{-15}$, $Al_2O_3{}^{-28}$ and $Al_2O_3{}^{-40}$ are silica-alumina with alumina contents of 15% by weight, 28% by weight and 40% by weight respectively. 600 × 8 hr. means the calcination conducted at 600° C. for 8 hours. The curves without the calcination conditions indicated represent uncalcined silica-alumina.

DESCRIPTION OF THE INVENTION

The synthetic silica-alumina that is used in the process according to the invention is high-alumina synthetic silica-alumina represented by the formula $Al_2O_3 \cdot (SiO_2)_n \cdot mH_2O$ wherein $1.70 \leq n < 6.79$ which has an alumina content from 20% by weight to 50% by weight.

In general, silica-alumina active as a solid acid catalyst has a structure with a number of pores and is therefore of a very large specific surface area usually in the order from 150 to 700 m²/g. When the silica-alumina is calcined, it is subjected to sintering which causes degradation of the porous structure with the result that the surface area is reduced. The catalysic activity will then be reduced. The tendency of the reduction is especially remarkable if moisture is present. The smaller the pore size of silica-alumina the intenser will be the sintering. The pore size of silica-alumina is related to an alumina content of silica-alumina. For example, the average radius of pores is 16 Å for low-alumina silica-alumina with an alumina content from 8% by weight to 17% by weight and 28 Å for high-alumina silica-alumina with an alumina content from 20% by weight to 40% by weight.

When a low-alumina silica-alumina is calcined, reduction of the activity will be so great that it can no longer be used as the aralkylation catalyst in the process of the invention. On the contrary, when a high-alumina synthetic silica-alumina is calcined at a temperature from 450° C. to 600° C., the activity for the aralkylation reaction undergoes no reduction but the catalytic life is remarkably prolonged. Although the mechanism is not completely elucidated, it is believed that larger pore sizes of the high-alumina silica-alumina allow the silica-alumina to be hardly influenced by the sintering in such a way that the active sites for the aralkylation reaction are not decreased but those for the side reactions only are decreased with the result that reduction in the catalytic life due to the products of the side reactions is prevented.

The process of the invention is characterized by the use of silica-alumina with a high alumina content that has been calcined at a temperature within the specified range. Accordingly, the calcination of the catalyst is a critical factor.

The calcination treatment is satisfactory when conducted at a temperature from 450° C. to 600° C. for a period of time longer than 4 hours, and preferably up to 24 hours. The calcination may well be carried out in air and use of an inert gas is not needed.

The calcination temperature below 450° C. will give rise to no improvement of the life of catalytic activity, and calcination conducted at a temperature above 600° C. will be disadvantageous because of reduction in the activity due to sintering.

It is desirable to avoid the calcination temperature exceeding 600° C., even locally, in order to prevent sintering of catalysts from taking place. The presence of steam is not desirable during the calcination under the above-cited conditions. Steam will remarkably promote the sintering to cause reduction in the catalytic activity, though being variable depending upon the conditions used. It is therefore preferable to dry the silica-alumina thoroughly at a temperature from 150° C. to 200° C. prior to the calcination treatment.

The synthetic silica-alumina utilizable in the process of the invention may be prepared by any of the conventional deposition, coprecipitation and blending methods. For example, the method disclosed in U.S. Pat. Nos. 2,384,946 and 2,900,349 which involves obtaining silica-alumina gel by adding an aqueous solution of aluminum sulfate to a slurry of silica hydrogel from a slightly acidified aqueous solution of sodium silicate be preferably employed. The alumina content can easily be controlled by adjusting the added amount of the aluminum salt.

The alkylbenzenes with substituent alkyl group or groups containing 1–4 carbon atoms used in the process of the invention include $C_q$ and $C_{10}$ aromatics such as toluene, ethylbenzene, o-, m- and p-xylenes, cumene, o-, m- an p-methylethylbenzenes, and 1,2,3-, 1,2,4 and 1,3,5-trimethylbenzenes. They may be used either in mixture or in isolated component. Number of the carbon atoms in the alkyl group or groups over 4 is not recommendable, because dealkylation will then occur more readily to result in lower yield of the desired product. Benzene is not usable from the industrial point of view because of the low reaction yield. Alkylbenzene source containing o- or m-dialkylbenzenes or 1,2,4-trialkylbenzenes gives a favorable result in the process according to the invention, because it is reacted with styrenes in a better reaction yield. The other reactant, namely, styrenes are styrene, α-methylstyrene and vinyltoluenes. They may be used alone or in mixture.

As another starting material preferably utilized in the process of the invention are mentioned aromatic by-product oils in the thermal cracking of petroleum hydrocarbons at a temperature of 700° C. or higher with the object of mainly obtaining ethylene. Said aromatic by-product oils are a mixed oil with carbon atoms from 5 to 10 containing saturated aliphatic hydrocarbons in the range from 5 to 15% by weight, aromatic hydrocarbons other than aromatic olefins which are alkylbenzenes in the range from 35 to 85% by weight, unsaturated hydrocarbons in the range from 2 to 10% by weight and aromatic olefins in the range from 2 to 15% by weight, although they are variable depending upon the nature of the starting oil fed to the cracking equipment and the cracking temperature. Preferably employed in process of the invention among said by-product oils is a distillate containing components with a boiling range from 135° C. to 198° C. That is to say, the distillate that is substantially a mixture of $C_8$–$C_{10}$ aromatic hydrocarbons is preferably employed. An analysis of the distillate as mentioned above is illustrated in the Table below.

|  | n-Paraffins | iso-Paraffins | Naphthene | Aromatic hydrocarbons | Olefins | Total |
|---|---|---|---|---|---|---|
| $C_8$ | 0.3 | 0.3 | 1.8 | 43.0 | 22.9 | 68.3 |
| $C_9$ | 0.3 | 0.3 | 0.3 | 18.0 | 10.1 | 29.0 |
| $C_{10}$ | 0.0 | 0.0 | 0.3 | 1.2 | 1.2 | 2.7 |
| Total | 0.6 | 0.6 | 2.4 | 62.2 | 34.2 | 100.0 |

(% by weight)

Olefins in the above-cited $C_8$–$C_{10}$ distillate are, for the most part, aromatic olefins which are styrenes, and they are starting materials preferably utilized for the present invention. The $C_8$–$C_{10}$ distillate as mentioned above may be a preferable starting material for the invention either in mixture or in isolated component with a given carbon number.

Conditions under which the process of the invention is carried out will be described below.

The reaction temperature is usually in the range from 100° C. to 200° C., although it is variable depending upon the nature of the styrenes and alkylbenzenes employed. Temperatures beyond the above-cited range is not recommendable, because at temperatures below 100° C. will be associated the desired aralkylation with polymerization of the styrene, and use of temperatures over 200° C. will cause decomposition of the aralkylated alkylbenzenes formed. More preferred temperatures are in the range from 140° C. to 160° C.

The reaction pressure may be a pressure sufficiently high to maintain the reaction zone in liquid phase. The pressure is not an essential condition provided that the above-mentioned requirement to maintain liquid phase is met. It is usually preferred to carry out the reaction at a pressure from 3 kg./cm$^2$ to 10 kg/cm$^2$, although the reaction pressure may of course be varied depending upon the nature of the starting materials and the reaction temperature employed.

If the reaction zone contains gas phase, polymerization of the styrene will be accelerated over the catalyst in the gaseous area so that not only the styrene yield will be decreased but also the life of the catalyst will be shortened due to surface of the catalyst covered with the polymer.

The time kept in contact with the catalyst in the reaction zone is in the range from 0.5 l. styrene/l. catalyst/hr. to 0.02 l. styrene/l. catalyst/hr. and preferably from 0.3 l. styrene/l. catalyst/hr. to 0.05 l. styrene/l. catalyst/hr.

It is preferred that amount of the styrenes continuously fed to the catalyst layer is 15% by weight or smaller. In such a case, temperature rise due to heat of the aralkylation reaction is 55° C. or smaller. Temperature rise more than the above will unfavorably cause undesired side reactions such as polymerization of the styrenes and decomposition of the aralkylation products. Usually for adjustment of the above amount of the styrenes employed is adjustment of the styrenes concentration at the inlet to the catalyst layer by means, for example, of dilution with an excess amount of the alkylbenzenes or recycle of the reaction products at the outlet from the catalyst layer. However, it is not recommendable to achieve the object by adjusting the styrene concentration with a solvent inert to the reaction such as, for example, an aliphatic hydrocarbon or a halogenated hydrocarbon. Presence of a reaction inert component in the reaction system will promote dimerization of the styrene or cyclic dimerization of the styrene unfavorably with the result that the styrene dimer or the cyclic dimer such as indane derivatives is incorporated into the desired aralkylated alkylbenzene products.

Preferred products of the process according to the invention are the monostyrenated and distyrenated products. For example, in the case where xylenes and styrene are employed, there are produced a mixture of 1-xylyl-1-phenylethanes as the monostyrenated product and a mixture of various isomers which are adducts of one mole of the xylene and two moles of styrene as the distyrenated product.

Heavier oils other than these which are polymers of styrene are not desirable.

The monostyrenated products, distyrenated products and styrene polymers can be identified by measuring the ratio of aliphatic protons (abbreviated as PaH) to aromatic protons (abbreviated as ArH) by means of NMR.

|  | PaH | ArH | PaH/ArH |
|---|---|---|---|
| Monostyrenated product $C_{16}H_{18}$ | 10 | 8 | 1.25 |
| Distyrenated product $C_{24}H_{26}$ | 14 | 12 | 1.17 |
| Polymer $[C_8H_8]_n$ | 3xn | 5xn | 0.6 |

DESCRIPTION OF PREFERRED EMBODIMENTS

The invention will concretely be described below by examples. In the examples, styrene yield means the value in terms of percentage for moles of the styrene converted to monostyrenated and distyrenated products against moles of the styrene fed as the starting material. The larger the value the more favorable will be the results of the process.

Procedures in the examples were the same as in the following Reference Examples 1-4 unless otherwise indicated.

Reference Example 1 — Preparation of the Catalyst

By dissolving 168.8 g. of sodium silicate with silica:-sodium oxide ratio by weight of 2.9 in water is prepared 2 kg. of an aqueous solution of sodium silicate. While maintaining the solution at a temperature of 35 ± 1° C. with vigorous stirring, 70 g. of 40% sulfuric acid is added to it over a period of about 60 minutes. Cooling is required in order to keep the temperature not exceeding 35 ± 1° C. by the addition of sulfuric acid. After completion of the addition, stirring is continued for additional 2 hours for ageing. Then, a 20% by weight aqueous solution of aluminum sulfate is added with stirring over a period of 90 min. Amounts of the aqueous aluminum sulfate solution to be added correspond to the alumina content of the desired silica-alumina, the amounts being 222.5 gr., 490.4 gr. and 840.6 gr. respectively for the alumina contents of 15% by weight, 28% by weight and 40% by weight.

After completion of the addition of aluminum sulfate solution the resulting solution is weakly alkalized to pH 8.0–8.5 by the addition of 15% aqueous ammonia. The slurry after the addition of the aqueous ammonia is stirred for about 30 min. for ageing.

The slurry is then filtered, and the filtrate is washed with 2% aqueous solution of $NH_4Cl$. The filtration and the washing are repeated until the filtrate becomes neutral. The slurry filtrate is dried at a temperature of 200° C. for 8 hours and pulverized to particle sizes equivalent to 5–10 mesh screen.

In the examples and the reference examples were used three catalysts of alumina contents of 15% by weight, 28% by weight and 40% by weight. They are abbreviated as $Al_2O_3{}^{-15}$, $Al_2O_3{}^{-28}$ and $Al_2O_3{}^{-40}$, respectively.

Reference Example 2 — Calcination of the catalyst

For calcination of the catalyst was used an electric oven controlled at a set temperature within ±5° C. The catalyst is placed and dried in the electric oven set at a temperature of 150° C. After dried, the temperature is raised at a rate of 100° C./hour to a predetermined calcination temperature. After the temperature is raised, calcination is done at the temperature for 8 hours. After cooled, the resulting catalyst is used for the reaction.

Reference Example 3 — Reaction Experiments

The catalyst is packed in a cylindrical pressure vessel to prepare a cylindrical catalyst layer 40 mm. in diameter, 200 mm. in length and 250 ml. in volume. The vessel is covered with a lagging material of a thickness of 1.5 cm. and placed in the constant temperature bath of which the heating system is a thermostat controlled by a set temperature within ±1° C. An alkylbenzene-styrene mixture is continuously fed to the catalyst layer by means of a constant-flow pump, and reactor effluent are collected in a pressure receiver after cooled pressured to a pressure of 7 kg./cm² of nitrogen. The reactor effluent (distillation feedstuff) are discharged at a predetermined interval, and the products are separated by distillation. Results of the distillation for each component are shown in terms of the composition on average in 10 days from initiation of the reaction unless otherwise indicated.

Reference Example 4 — Estimation of the Life of the Catalyst-Measurement of Bromine Number (BrNo)

Experiments for the life of the catalyst were carried out using an apparatus similar to the above-mentioned one but with a smaller catalyst layer 16 mm. in diameter, 20 cm. in length and 40 ml. in volume. The catalyst was used in 10–18 meshes. The feedstuff which was a mixture in a ratio of the alkylbenzenes 10 moles:the styrenes 1 mole is fed at a reaction temperature of 150° C.

The styrene has a BrNo of 154, and the feedstuff is fed to the reaction in a dilution to a BrNo of 13.8. During the period of time when the catalytic activity is high, the BrNo of the distillate is 0.05 or lower. When the catalytic activity has been lost, BrNo of the effluent is rapidly increased so that the life of the catalyst can be estimated. The reaction ratio is expressed in terms of the BrNo:

$$\text{BrNo reaction ratio} \frac{\text{BrNo of the effluent}}{\text{BrNo of the feedstuff}}$$

Examples 1–4 and Comparative Examples 1 and 2

Experiments — Reaction between o-xylene and Styrene-Effect of calcination

Results of experiments as to reaction of o-xylene with styrene catalyst using the procedures as set forth in Reference Examples 1–3 are shown in Table 1. The results indicate that calcination improves the styrene yield.

The reaction products were separated by distillation under reduced pressure after unreacted xylene had been removed by distillation under normal pressure. The monostyrenated product is a fraction distilling at temperatures in the range from 135° C. to 150° C. at 3 mm.Hg which is identified by NMR analysis and has a proton ratio PaH/ArH of 1.27–1.22. The distyrenated product is a fraction distilling at temperatures in the range from 180° C. to 220° C. at 3 mm.Hg which has a PaH/ArH of 1.19–1.14 according to NMR. The heavier residue is styrene polymers with a PaH/ArH of 0.62–0.59 according to NMR.

Table 1

| | Example 1 | Example 2 | Example 3 | Example 4 | Comparative Example 1 | Comparative Example 2 |
|---|---|---|---|---|---|---|
| Catalyst | $Al_2O_3^{-40}$ | $Al_2O_3^{-28}$ | $Al_2O_3^{-28}$ | $Al_2O_3^{-28}$ | $Al_2O_3^{-40}$ | $Al_2O_3^{-28}$ |
| Calcination | 550° C. | 550° C. | 600° C. | 450° C. | None | None |
| Reaction temperature | 145° C. | 150° C. | 150° C. | 150° C. | 145° C. | 150° C. |
| Xylene : styrene molar ratio | 10:1 | 10:1 | 10:1 | 10:1 | 10:1 | 10:1 |
| Amount fed ml./hr. | 250 | 250 | 250 | 250 | 250 | 250 |
| Starting material for distillation | 2340 g. | 2340 g. | 2340 g. | 2340 g. | 2340 g. | 2340 g. |
| Monostyrenated product (g.) | 279 | 287 | 292 | 251 | 216 | 246 |
| Distyrenated product (g.) | 52 | 52 | 61 | 73 | 69 | 76 |
| Residue (g.) | 30 | 14 | 18 | 30 | 50 | 40 |
| Styrene yield (%) | 85 | 93 | 91 | 85 | 75 | 80 |

Examples 5–9 and Comparative Examples 3–8

Estimation of the Life of the Catalyst

Reactions were carried out in accordance with Reference Examples 1–3 using o-xylene and styrene as the reactants. Life of the catalyst was measured by the method described in Reference Example 4. As clearly seen from FIG. 1 of the attached drawing and Table 2 below, effect of the calcination is clear with high-alumina containing 20%–50% alumina.

The life of the catalyst was indicated with reference to the point at which the reaction in terms of BrNo was 85% or below.

Table 2

| Calcination conditions and life of the catalyst. | | | |
|---|---|---|---|
| Example | Catalyst | Calcination conditions | Life in day |
| 5 | $Al_2O_3^{-28}$ | 600° C. × 8 hours | 34 |
| 6 | $Al_2O_3^{-40}$ | 600° C. × 8 hours | 30 |
| Comparative Example | | | |
| 3 | $Al_2O_3^{-28}$ | Non-calcinated | 15 |
| 4 | $Al_2O_3^{-40}$ | Non-calcinated | 13 |
| 5 | $Al_2O_3^{-15}$ | Non-calcinated | 6 |
| 6 | $Al_2O_3^{-28}$ | 700° C. × 8 hours | 10 |
| 7 | $Al_2O_3^{-28}$ | 350° C. × 8 hours | 16 |
| 8 | $Al_2O_3^{-15}$ | 600° C. × 8 hours | 12 |
| Example | | | |
| 7 | $Al_2O_3^{-28}$ | 600° C. × 8 hours | 30 |
| 8 | $Al_2O_3^{-28}$ | 550° C. × 8 hours | 34 |
| 9 | $Al_2O_3^{-28}$ | 450° C. × 8 hours | 26 |

Examples 10–14

Reactions were carried out between various alkylbenzenes and styrene in accordance with Reference Examples 1–3 using $Al_2O_3^{-28}$ as the catalyst. The calcination was done at 550° C. for 8 hours. The reaction temperature was 150 °C., the alkylbenzene:styrene molar ratio was 10:1, and sv. was 1.0. Products after distillation were identified by means of NMR. The results are shown in Table 3.

Table 3

| Example | 10 | 11 | 12 | 13 | 14 |
|---|---|---|---|---|---|
| Alkylbenzene | m-xylene | Mixed xylenes | Pseudo-cumene | $C_9$-aromatics | $C_{10}$-aromatics |
| Starting material for distillation (g.) | 2340 | 2340 | 2350 | 2350 | 2380 |
| Monostyrenated product (g.) | 299 | 279 | 316 | 295 | 298 |
| Distyrenated product (g.) | 56 | 52 | 57 | 54 | 53 |
| Heavier residue (g.) | 18 | 30 | 20 | 32 | 40 |
| Styrene yield (%) | 91 | 85 | 89 | 84 | 80 |

Examples 15 and 16

Reactions were carried out between o-xylene and α-methylstyrene, or m-, p-vinyltoluenes in accordance with Reference Examples 1–3 using $Al_2O_3^{-28}$ as the catalyst. Calcination of the silica-alumina was done at 550° C. for 8 hours, the reaction temperature was 150° C., the molar ratio was 10:1, and sv. was 1.0. The results are shown in Table 4.

Table 4

| Example | 15 | 16 |
|---|---|---|
| Syrenes | α-Methylstyrene | m-, p-vinyltoluene |
| Starting material for distillation (g.) | 2350 | 2350 |
| Monostyrenated product (g.) | 314 | 292 |
| Distyrenated product (g.) | 50 | 63 |
| Heavier residue (g.) | 30 | 32 |
| Styrene yield (%) | 87 | 86 |

Example 17

The following procedures were carried out in accordance with Reference Examples 1–3:

A fraction distilling out at temperatures of 135° C.–198° C. was separated from the thermal cracked by-product oil in a cracking step of naphthene source. Composition of the distillate was: saturated aliphatics 3.6% by weight, aromatics (excluding styrenes) 62.2% by weight and unsaturated hydrocarbons 34.2% by weight (including styrenes 32.2% by weight).

The reactant was prepared by mixing 3 parts by weight of xylenes with 1 part by weight of said distillate. The feeding rate was 250 ml./hr., the reaction temperature 150° C., the catalyst $Al_2O_3^{-40}$ and the calcination conditions 550° C. × 8 hours. The results are shown in Table 5.

Example 18

The following procedures were carried out in accordance with Reference Examples 1–3.

A styrene-containing xylene fraction distilling out at temperatures of 135° C.–145° C. was separated by distillation from the thermal cracked by-product oil in a cracking step of naphthene source. Composition of said xylene distillate was:

| Non-Aromatics | 3.7% by weight |
|---|---|
| Toluene | 0.1 |
| Ethylbenzene | 9.6 |
| p-xylene | 19.2 |
| m-xylene | 27.8 |
| o-xylene | 10.6 |
| Styrene | 28.8 |
| Cumene | 0.2 |

The reactant was prepared by mixing 3 parts by weight of xylenes with 1 part by weight of said xylene distillate. The other conditions were the same as in Example 17. The results are shown in Table 5.

Table 5

| Example | 17 | 18 |
|---|---|---|
| Starting material for distillation (g.) | 3000 | 3000 |
| Monostyrenated product (g.) | 330.0 | 314.1 |
| Distyrenated product (g.) | 79.4 | 78.3 |
| Residue (g.) | 38.5 | 8.6 |

We claim:

1. In the reaction wherein an alkylbenzene or alkylbenzenes containing in the substituent alkyl group or groups from 1 to 4 carbon atoms in total is aralkylated with at least one styrene selected from the group consisting of styrene, vinyltoluenes and α-methylstyrene a process which comprises carrying out the reaction by continuously feeding to a catalyst layer the above-mentioned alkylbenzene or alkylbenzenes and styrene sources in liquid phase at a temperature from 100° C. to 200° C., said catalyst layer consisting essentially of synthetic silica-alumina containing from 20% by weight to 50% by weight alumina that has been calcined at a temperature in the range from 450° C. to 600° C.

2. Process according to claim 1 wherein the above-mentioned alkylbenzene or alkylbenzenes and styrene sources are a distillate in the boiling range from 135° C. to 198° C. of the thermal cracked by-product oil from the cracking of petroleum hydrocarbons at a temperature of 700° C. or higher.

3. Process according to claim 1 or 2 wherein the alkylbenzene and styrene sources to be continuously fed are of a styrene content of 15% by weight or lower.

* * * * *